(12) United States Patent
Hung et al.

(10) Patent No.: US 8,399,675 B2
(45) Date of Patent: Mar. 19, 2013

(54) COMPOUNDS AND PREPARATION FOR MONTELUKAST SODIUM

(75) Inventors: Jui-Te Hung, Taoyuan (TW); Ching-Peng Wei, Taoyuan (TW)

(73) Assignee: Formosa Laboratories, Inc., Taoyuan (TW)

( * ) Notice: Subject to any disclaimer, the term of this patent is extended or adjusted under 35 U.S.C. 154(b) by 367 days.

(21) Appl. No.: 12/709,882

(22) Filed: Feb. 22, 2010

(65) Prior Publication Data
US 2010/0152453 A1      Jun. 17, 2010

Related U.S. Application Data

(62) Division of application No. 11/552,419, filed on Oct. 24, 2006, now Pat. No. 7,700,776.

(51) Int. Cl.
*C07D 215/18* (2006.01)
*C07D 263/12* (2006.01)

(52) U.S. Cl. .................................. 546/180; 548/237
(58) Field of Classification Search .................. None
See application file for complete search history.

(56) References Cited

U.S. PATENT DOCUMENTS

| 4,770,803 A * | 9/1988 | Forsberg ................... 252/75 |
| 5,438,141 A * | 8/1995 | LaBell et al. ................ 546/176 |
| 2005/0187243 A1* | 8/2005 | Niddam-Hildesheim et al. ........................ 514/311 |

FOREIGN PATENT DOCUMENTS

| WO | WO2006008751 | * | 1/2006 |
| WO | WO2007069261 | * | 6/2007 |

* cited by examiner

*Primary Examiner* — Jason M Nolan
*Assistant Examiner* — Po-Chih Chen
(74) *Attorney, Agent, or Firm* — WPAT, P.C.; Anthony King

(57) ABSTRACT

This invention relates to novel compounds and a process for preparation of montelukast sodium.

2 Claims, 4 Drawing Sheets

COMPOUNDS AND PREPARATION FOR MONTELUKAST SODIUM

CROSS-REFERENCE TO RELATED APPLICATIONS

This application is a Divisional of the pending U.S. patent application Ser. No. 11/552,419 filed on Oct. 24, 2006, all of which is hereby incorporated by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

This invention relates to novel compounds and a process for preparation of montelukast sodium.

DESCRIPTION OF PRIOR ART

The chemical name of montelukast sodium is: Sodium 1-[[[(1R)-1-[3-[(1E)-2-(7-chloro-2-quinolinyl)ethenyl]phenyl]-3-[2-(1-hydroxy-1-methylethyl)phenyl]propyl]thio]methyl]cyclopropaneacetic acid and its structure is represented as follows:

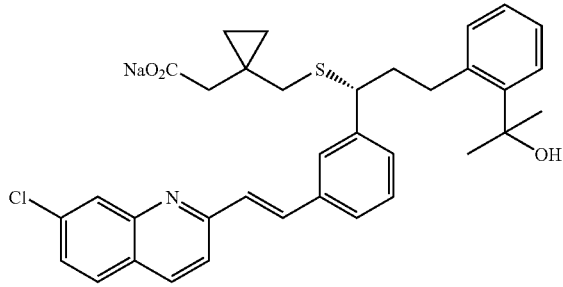

Montelukast sodium is a leukotriene antagonist and inhibits the leukotriene biosynthesis. It is a white to off-white powder that is freely soluble in methanol, ethanol, and water and practically insoluble in acetonitrile.

European Patent No. 480,717 discloses montelukast sodium and its preparation starting with the hydrolysis of its ester derivative to the crude sodium salt, acidification of the crude to montelukast acid, and purification of the crude acid by column chromatography to give montelukast acid as an oil. The resulting crude oil in ethanol was converted to montelukast sodium by the treatment with an equal molar aqueous sodium hydroxide solution. After removal of the ethanol, the montelukast sodium was dissolved in water and then freeze dried. The montelukast sodium thus obtained is of a hydrated amorphous form as depicted in FIG. 2.

The reported syntheses of montelukast sodium, as pointed out by the inventor in EP 737,186, are not suitable for large-scale production, and the product yields are low. Furthermore, the final products, as the sodium salts, were obtained as amorphous solid which are often not ideal for pharmaceutical formulation. Therefore, they discloses an efficient synthesis of montelukast sodium by the use of 2-(2-(3-(S)-(3-(7-chloro-2-quinolinyl)ethenyl)phenyl)-3-methanesulfonyloxypropyl)phenyl)-2-propanol to couple with the dilithium salt of 1-(mercaptomethyl)cyclopropaneacetic acid. The montelukast acid thus obtained is converted to the corresponding dicyclohexylamine salt and recrystallized from a mixture of toluene and acetonitrile to obtain crystalline montelukast sodium. This process provides improved overall product yield, ease of scale-up, and the product sodium salt in crystalline form.

According to the process described in EP 737,186, the chemical as well as optical purities of montelukast sodium depends very much on the reaction conditions for the mesylation of the quinolinyl diol with methanesulfonyl chloride. For instance, the reaction temperature determinates the chemical purity of the resulting coupling product montelukast lithium, due to the fact that an increase in the reaction temperature resulted in decreased selectivity of mesylation toward the secondary alcohol. Mesylation of the tertiary alcohol occurred at higher temperature will produce, especially under acidic condition, the undesired elimination product, the styrene derivative. This styrene impurity is difficult to remove by the purification procedure using DCHA salt formation; while excess base, butyl lithium in this case, present in the reaction mixture causes the formation of a cyclization by-product, which will eventually reduce the product yield.

PCT WO 2005/105751 discloses an alternative process for preparing montelukast sodium by the coupling of the same mesylate as disclosed in '186 patent with 1-(mercaptomethyl)cyclopropane alkyl ester in the presence of a base. In this patent, the base butyl lithium, a dangerous and expensive reagent, is replaced with other milder organic or inorganic base. However, the problem concerning the formation of the styrene impurity is still not resolved.

SUMMARY OF THE INVENTION

The present invention provides a process for preparing montelukast sodium, which comprises reacting sodium alkoxide with montelukast acid in an organic solvent, wherein montelukast acid is obtained by acidification of montelukast cyclohexylamine.

The present invention also provides a novel compound {1-[(4,4-dimethyl-4,5-dihydro-1,3-oxazol-2-yl)methyl] cyclopropyl}methanethiol.

The present invention further provides novel compounds of formulae III, IV and V.

DETAILED DESCRIPTION OF THE INVENTION

Figure 1:
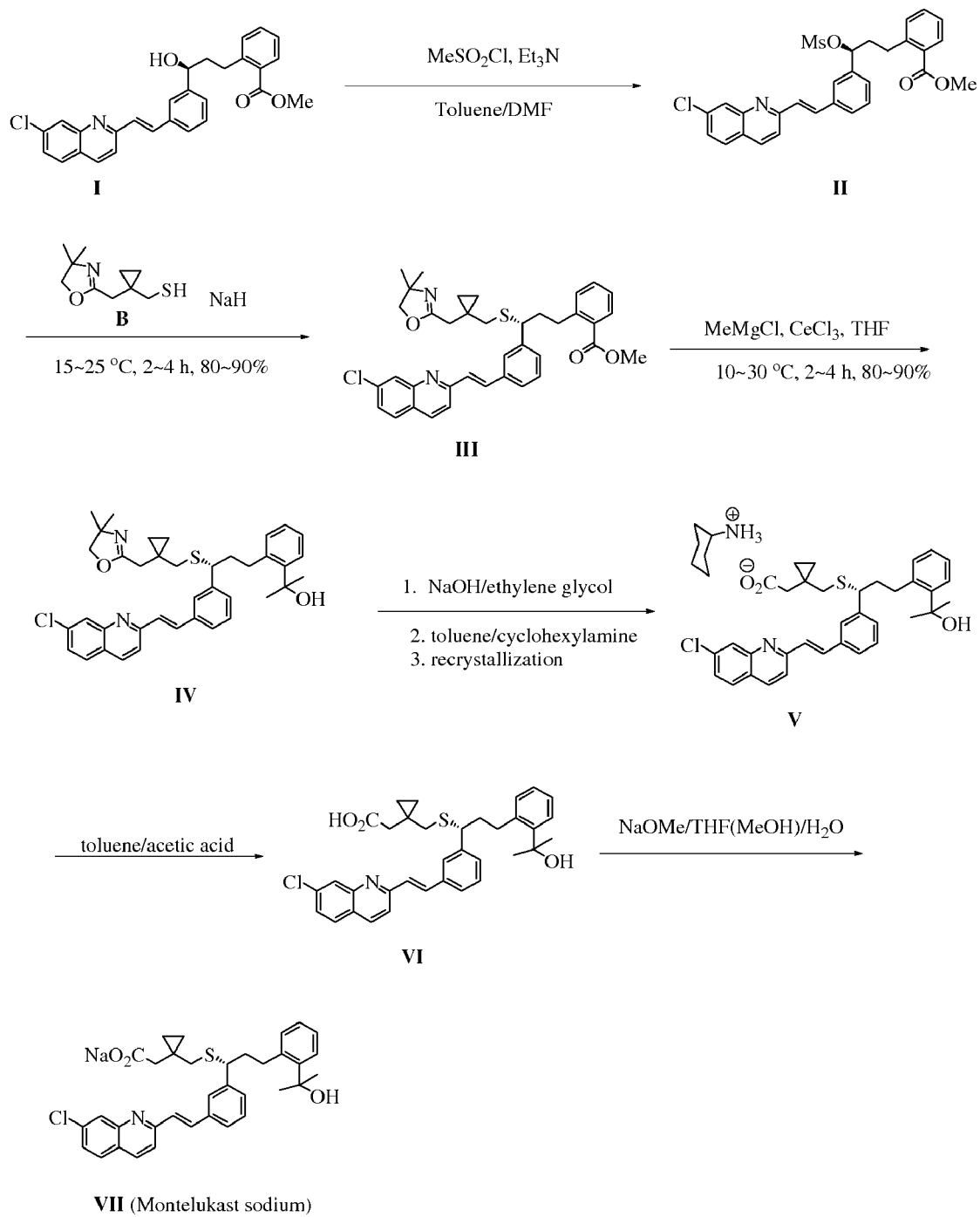
FIG. 1 shows the synthesis of the present invention.
Figure 2:
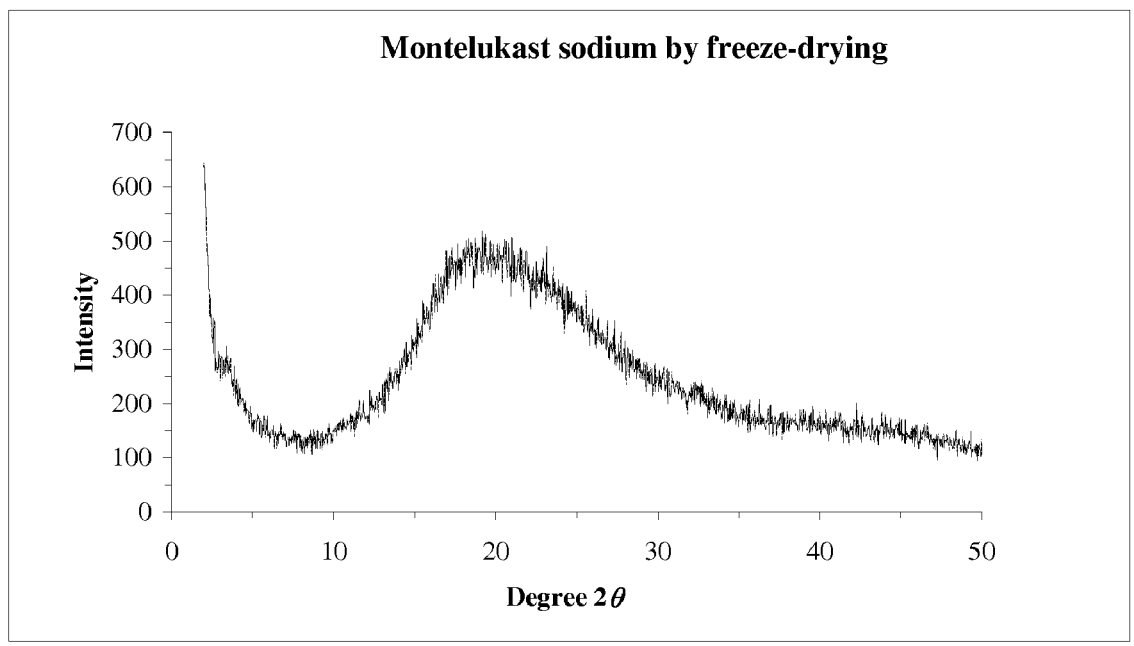
FIG. 2 illustrates the XRPD of amorphous montelukast sodium obtained by the freeze-drying method.
Figure 3:
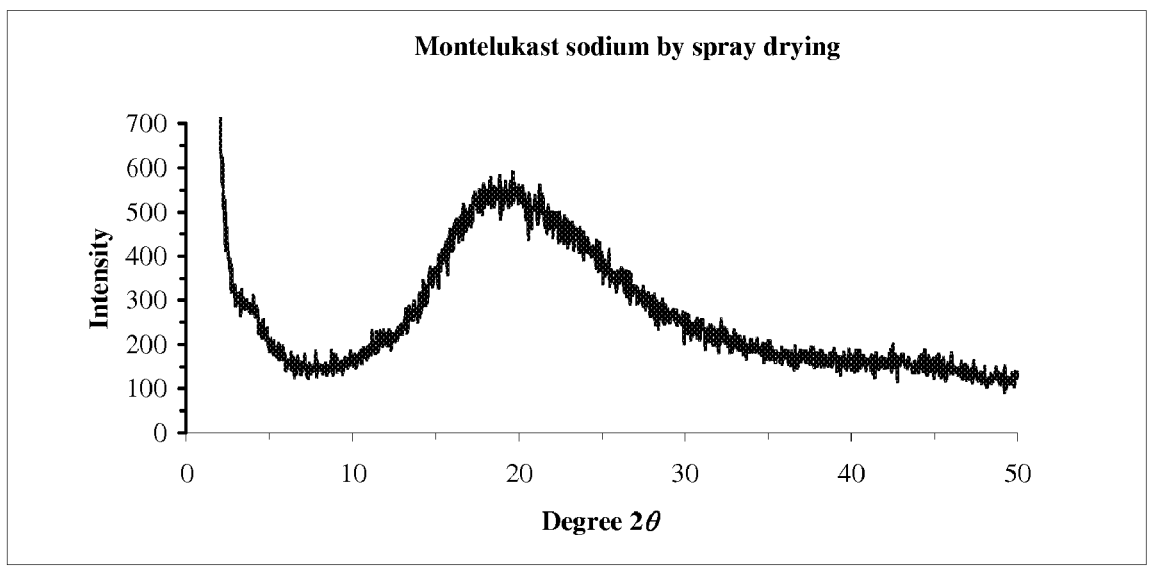
FIG. 3 illustrates the XRPD of amorphous montelukast sodium obtained by the current spray drying method.

The present invention provides a novel process for the preparation of montelukast sodium free of styrene and lactone impurities, and an overall yield comparable with that disclosed in EP 737,186. Also, the present invention provides a process without isolation of the unstable mesylate and an easier operation on the subsequent coupling reaction at higher reaction temperature. The deprotection of the oxazoline function provides a crude montelukast sodium. After acidic work-up, a crude montelukast acid is obtained and is purified by the formation and crystallization of its corresponding cyclohexylamine salt. The crystalline salt is freed to provide an acid and is re-dissolved in THF or methanol and is then converted to montelukast sodium by the treatment with an equal molar sodium methoxide. After distillation to remove most solvents, the crude is diluted with water and then spray-dried to afford montelukast sodium in an amorphous form as depicted in FIG. 3.

Accordingly, the present invention provides a process for preparing montelukast sodium, which comprises reacting sodium alkoxide with montelukast acid in an organic solvent, wherein montelukast acid is obtained by acidification of montelukast cyclohexylamine salt.

In the process of the present invention, sodium alkoxide is not limited but can be selected from the group consisting of sodium methoxide, sodium ethoxide, sodium propoxide, and sodium butoxide. In the preferred embodiment, the sodium alkoxide used is sodium methoxide.

In the process of the present invention, montelukast cyclohexylamine is not limited but to in a form of crystalline salt, which provides montelukast acid.

In the process of the present invention, the organic solvent is not limited but selected from tetrahydrofuran (THF) or methanol.

To facilitate drying of montelukast sodium, the process of the present invention further comprises (i) removing the organic solvent; (ii) adding water to form an aqueous solution; and (iii) drying the aqueous solution to produce montelukast sodium in an amorphous form.

In the process of the present invention, montelukast cyclohexylamine is obtained by the reaction of cyclohexylamine and montelukast acid, and the above montelukast acid is obtained by a deprotection of the oxazoline function of compound of formula IV followed by acidification.

IV

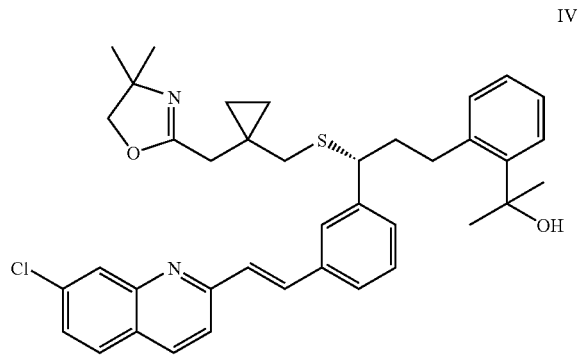 [SMILES: CC1(C)COC(CC2(CS[C@H](CCc3ccccc3C(C)(C)O)c3cccc(/C=C/c4ccc5ccc(Cl)cc5n4)c3)CC2)=N1]

In a preferred embodiment, the deprotection is made by a base (such as sodium hydroxide) in an organic solvent (such as ethylene glycol).

In the process of the present invention, the compound of formula IV is prepared by reacting a compound of formula III

III

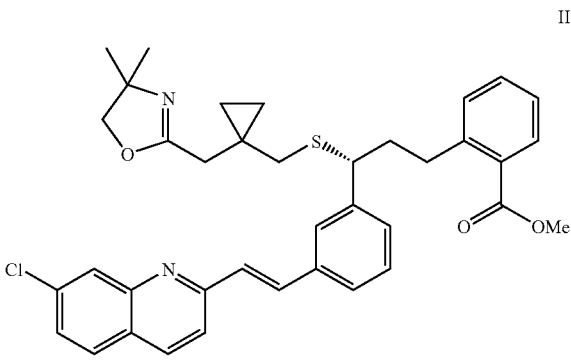

with methylmagnesium halide in the presence of cerium chloride in THF.

In a preferred embodiment, the preparation is made with the addition of methylmagnesium halide in the range of 2.5~4.0 equivalents and in the presence cerium chloride in more than 1.0 equivalent.

In the process of the present invention, the compound of formula III is prepared by the coupling of a compound of formula B

B

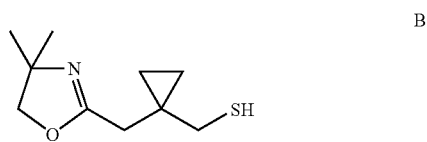

with a compound of formula II.

II

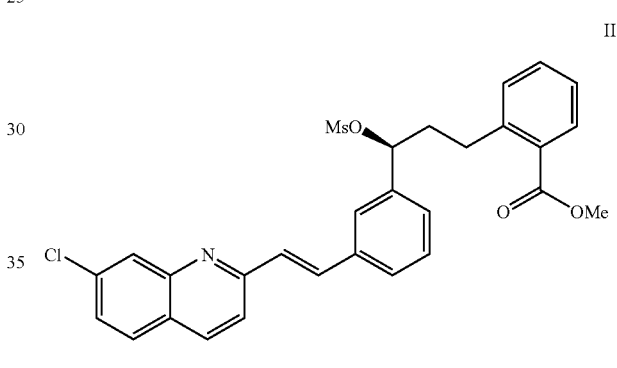

In a preferred embodiment, the coupling is performed in the temperature range of −5~25° C.

The present invention also provides {1-[(4,4-dimethyl-4,5-dihydro-1,3-oxazol-2-yl)methyl]cyclopropyl}methanethiol.

The present invention further provides a compound of formula III which is represented as

III

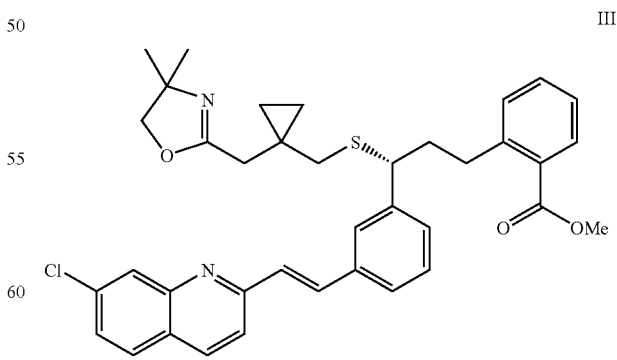

The present invention further provides a compound of formula IV which is represented as

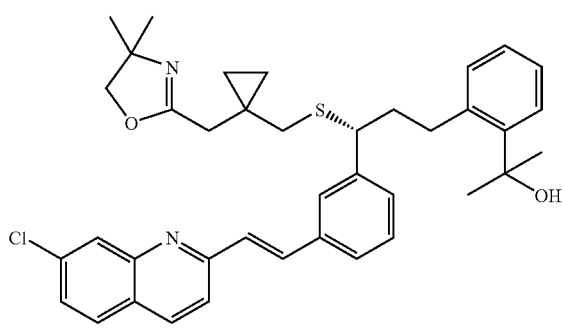

IV

The present invention further provides a compound of formula V which is represented as

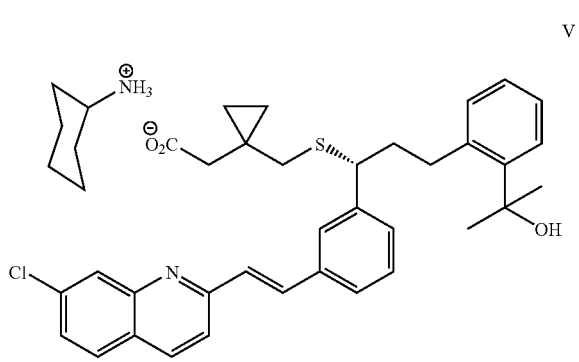

V

Figure 4:
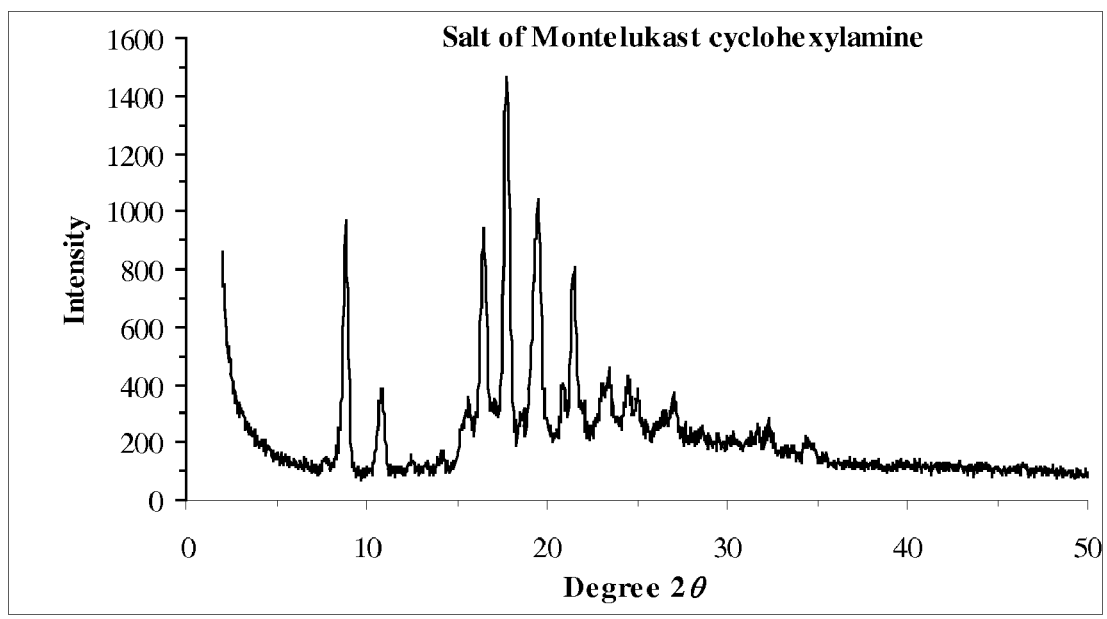
FIG. 4 illustrates the XRPD of crystalline montelukast cyclohexylamine.

The compound of formula V has a powder XRD as shown in FIG. 4.

EXAMPLE

The examples below are non-limiting and are merely representative of various aspects and features of the present invention.

Example 1

Preparation of mesylate II and oxazoline III: In a reactor equipped with mechanic stirrer, thermocouple, and feeding tank was charged under nitrogen with a wet cake of compound I in toluene (11 parts). After azeotropic distillation (6 parts), the mixture was sampled for water content test (KF<0.1%). To the resulting mixture after cooling to room temperature was added DMF (1.7 parts) and triethylamine (2 equiv.). When the addition was complete, the reactor was cooled to −5~5° C. Methanesulfonyl chloride (1.5 equiv.) diluted with toluene (2 parts) in the feeding tank was added dropwise and the pot temperature controlled in the range of −5.0~5.0° C. during the addition. After the addition was complete, the mixture was kept stirring at −5.0~5.0° C. until mesylation was complete. During this time into another SS reactor was charged under nitrogen toluene (2 parts), DMF (0.5 parts), sodium hydride (60%, 3.0 equiv.), and oxazoline B (1.2 equiv.) while keeping the pot temperature below 20.0° C. The mesylate in the GL reactor was added through a pipeline to the SS reactor containing the sodium salt of oxazoline B. Two hours after the addition, the mixture was sampled and analyzed by HPLC (compound III>95.0%). The reaction mixture was quenched with chilled water (5 parts), and the organic layer is separated and washed with brine. The organic layer was concentrated until dryness to afford compound III as an oil in 80~96% yield (see Table 1). $^1$H NMR (600 MHz, CDCl$_3$) δ 7.12~7.97 (15 H, Ar), 3.84 (t, J=7.3 Hz, SCH, 1 H), 3.76 (s. CH$_2$O, 2 H), 3.73 (s, OCH$_3$, 3 H), 3.00 and 2.85 (m, SCHCH$_2$, 2 H), 2.42 and 2.39 (ABq, $^2$J=13.0 Hz, 2 H), 2.34 and 2.29 (ABq, SCH$_2$, $^2$J=14.9 Hz, 2 H), 2.06~2.18 (m, 2 H), 1.13 (s, CH$_3$, 6 H), 0.28~0.48 (m, 4 H). $^{13}$C NMR (150 MHz, CDCl$_3$): δ 167.8, 164.2.0, 156.8, 148.6, 143.6, 143.3, 136.4, 136.0, 135.4, 135.0, 132.0, 131.0, 130.8, 129.4, 128.9, 128.8, 128.7, 128.61, 128.58, 128.1, 127.0, 126.9, 126.0, 125.6, 119.5, (Ar), 78.7, 66.7, 51.9, 50.0, 39.2, 38.6, 34.1, 32.8, 28.4 (CH$_3$), 17.5 (Cy-C), 12.5, 12.2 (Cy-CH$_2$). FABMS (m/z, intensity): M$^+$ (639, 63.01%), M$^+$-C$_{10}$H$_{17}$NOS (B) (440, 8.69%), B$^+$—H (198, 100.00%). Other conditions used to prepare compound III were listed in Table 1.

TABLE 1

| | Conditions for the preparation of compound III | | | | | | | |
|---|---|---|---|---|---|---|---|---|
| Entry | Comp. I (eq.) | MeSO$_2$Cl (eq.) | Et$_3$N (eq.) | NaH (eq.) | Temp. (° C.) | Time (h.) | Purity (%) | Yield (%) |
| 1 | 1.0 | 1.5 | 2.0 | 4.0 | 15~20 | 5 | 96 | 85 |
| 2 | 1.0 | 1.2 | 1.5 | 2.5 | 15~20 | 2 | 98 | 91 |
| 3 | 1.0 | 1.5 | 2.0 | 3.0 | 5~10 | 2 | 99 | 86 |
| 4 | 1.0 | 1.5 | 2.0 | 2.2 | 5~10 | 4 | 96 | 96 |
| 5 | 1.0 | 1.2 | 1.5 | 3.0 | 0~5 | 2 | 98 | 80 |

Example 2

Preparation of IV: In a SS reactor equipped with mechanic stirrer, thermocouple, and feeding tank was charged under nitrogen THF (12 parts) and anhydrous CeCl$_3$ (2.5 equiv. KF<1.0%). The suspension was stirred at room temperature, and methylmagnesium chloride (3.0~3.5 equiv.) was added via a Teflon pump. After the addition was complete, the mixture was stirred further for 60 min, and cooled down to 10~25. Compound III in THF was then added through the feeding tank. After the addition, the mixture was allowed to react further for 2~4 h, and checked by HPLC (compound IV >95.0%). The reactor was cooled to 5.0~15.0° C., and water was carefully added. The precipitated solid was centrifuged and washed with THF, and the filtrate was concentrated to afford compound IV as an oil in 80~95% yield (see Table 2). $^1$H NMR (600 MHz, CDCl$_3$): δ 7.05~8.00 (15 H, Ar), 3.93 (t, J=7.3 Hz, SCH, 1 H), 3.78 (s, OCH$_2$, 2 H), 3.15 and 2.94 (m, SCH$_2$CH$_2$, 2 H), 2.43 and 2.35 (dd, 2 H), 2.33 and 2.29 (dd, 2 H), 2.16~2.27 (m, 2 H), 1.57 (s, 3 H), 1.56 (s, 3 H), 1.15 (s, CH$_3$, 6 H), 0.31~0.49 (m, 4 H). $^{13}$C NMR (150 MHz, CDCl$_3$): δ 164.6, 156.8, 148.6, 145.7, 144.0, 140.2, 136.4, 136.1, 135.5, 135.1, 131.4, 128.9, 128.7, 128.58, 128.56, 128.1, 127.03, 126.97, 126.92, 126.0, 125.62, 15.57, 125.4, 119.6 (olefinic), 78.9, 73.3, 66.8, 50.2, 39.6, 39.2, 34.0, 32.1, 32.0, 31.9, 28.42, 28.41, 17.5, 12.6, 12.3. FABMS (m/z, relative intensity): $M^+$ (639, 68.63%), $M^+$-$H_2O$ (621, 10.37%), $M^+$-B (440, 20.71%), $M^+$-B—$H_2O$ (424, 20.71%), $B^+$—H (198, 93.32%).

TABLE 2

Reaction conditions for the preparation of compound IV

| Entry | Comp. II (eq.) | CeCl$_3$ (eq.) | MeMgCl (eq.) | THF (parts) | Time (min.) | Temp. (°C.) | Purity (%) | Styrene (%) | Remaining II |
|---|---|---|---|---|---|---|---|---|---|
| 1 | 1.0 | 2.0 | 3.5 | 15 | 30 | 18~22 | 95.6 | ND | 0.11 |
| 2 | 1.0 | 0.5 | 2.5 | 15 | 60 | 13~17 | 77.1 | ND | 19.4 |
| 3 | 1.0 | 0.1 | 2.6 | 15 | 40 | 18~22 | 37.2 | ND | 53.2 |
| 4 | 1.0 | 1.2 | 2.6 | 15 | 30 | 18~22 | 80.3 | ND | 0.4 |
| 5 | 1.0 | 2.1 | 3.5 | 15 | 30 | 18~22 | 96.4 | ND | 0.0 |
| 6 | 1.0 | 2.1 | 2.5 | 12 | 120 | 20~25 | 96.5 | ND | 0.0 |

Example 3

Preparation of crude montelukast sodium: To compound IV in ethylene glycol (10 parts) was added aqueous sodium hydroxide solution (1~3 N, 2.0 equiv.), and the resulting suspension was heated to 120~150° C. for 12 h followed by HPLC analysis (montelukast sodium >94.0%). The reaction mixture was cooled to 60~70° C. and then concentrated under vacuum to afford montelukast sodium as an oil in 60~80% yield (see Table 3). $^1$H NMR (600 MHz, CD$_3$OD): δ 6.94~8.44 (15 H, Ar), 3.92 (t, J=6.66 Hz, 1 H), 2.97 (dt, J=4.68 Hz, 12.0 Hz, 1 H), 2.71 (dt, J=4.56 Hz, 12.0 Hz, 1 H), 2.53 and 2.41 (ABq, $^2$J=12.8 Hz, 2 H), 2.28 and 2.20 (ABq, $^2$J=14.6 Hz, 2 H), 2.13 (m, 1 H), 2.03 (m, 1 H), 1.41 (s, 3 H), 1.40 (s, 3 H), 0.42 (m, 1 H), 0.35 (m, 1 H), 0.28 (m, 1 H), 0.20 (m, 1 H). $^{13}$C NMR (150 MHz, CDCl$_3$): δ 180.9 (CO$_2$), 170.6, 158.9, 149.4, 147.2, 145.8, 141.4, 138.3, 137.9, 137.5, 137.0, 132.6, 130.6, 130.22, 130.19, 128.9, 128.4, 128.3, 128.1, 128.0, 127.4, 127.1, 126.7, 126.6, 120.97, 74.0 (ArC(CH$_3$)$_2$ OH), 51.6 (SCH), 44.8, 41.5, 41.2, 32.5, 32.0 (CH$_3$), 18.7 (Cy-C), 13.5, 13.0 (Cy-CH$_2$).

TABLE 3

Reaction conditions for the preparation of compound V

| Entry | Comp. IV (eq.) | NaOH (Conc. and eq.) | EG (parts) | Time (h.) | Temp. (°C.) | Product purity (%) |
|---|---|---|---|---|---|---|
| 1 | 1.0 | 1 N, 2 eq. | 10 | 25 | 120 | 97.2 |
| 2 | 1.0 | 1 N, 2 eq. | 10 | 12 | 130 | 97.5 |
| 3 | 1.0 | 3 N, 2 eq. | 10 | 5 | 150 | 94.0 |
| 4 | 1.0 | 4 N, 2 eq. | 5 | 4 | 160 | 90.8 |
| 5 | 1.0 | 3 N, 2 eq. | 10 | 3 | 195 | 62.0 |

Purification and Drying of Montelukast Sodium

Example 4

A crude oil of montelukast sodium was treated with 5% aqueous acetic acid to a pH of 5, and then extracted with toluene. The resulting toluene extract was washed with water. The organic layer containing montelukast acid was treated with cyclohexylamine (1.1~1.5 equiv.), and acetonitrile was added to effect precipitation. After stirring overnight, the salt was collected by filtration and washed with acetonitrile. The salt thus obtained was recrystallized over toluene/hexanes or toluene/acetonitrile until the desired purity was reached (see Table 4). The crystalline solid was analyzed by XRPD, and the spectrum is shown in FIG. 4. $^1$H NMR (600 MHz, CDCl$_3$): δ 7.06~8.04 (15 H, Ar), 6.41 (bs, cy-NH$_3^+$), 3.96 (t, J=7.08 Hz, 1 H), 3.15 (m, 1 H), 2.77~2.87 (m, 2 H), 2.57 and 2.51 (ABq, $^2$J=11.1 Hz, 2 H), 2.31 and 2.27 (ABq, $^2$J=15.0 Hz, 2 H), 2.22 (m, 1 H), 2.12 (m, 1 H), 1.95 (d, J=10.6 Hz, 2 H), 1.68 (d, J=12.9 Hz, 2 H), 1.56 (s, 3 H), 1.54 (s, 3 H), 1.28 (m, 2 H), 1.14 (m, 2 H), 1.08 (m, 2 H), 0.49 (m, 1 H), 0.42 (m, 1 H), 0.34 (m, 1 H), 0.27 (m, 1 H). $^{13}$C NMR (150 MHz, CDCl$_3$): δ 179.0 (CO$_2$), 157.0, 148.7, 145.6, 144.1, 140.5, 136.6, 136.3, 135.7, 135.4, 131.7, 129.1, 128.8, 128.7, 128.6, 128.2, 127.2, 127.1, 127.0, 126.2, 125.8, 125.7, 125.6, 119.7 (olefinic), 73.7, 50.3, 50.2, 43.7, 40.3, 40.1, 32.5, 32.1, 32.0, 31.8, 25.1, 24.7, 17.7, 13.1, 12.4.

TABLE 4

Recrystallization of Montelukast cyclohexylamine.

| Entry | solvents | Solvent volume by parts | Purity HPLC % |
|---|---|---|---|
| 1 | Toluene, acetonitrile | 5, 10 | 99.22 |
| 2 | Toluene, acetonitrile | 10, 15 | 99.03 |
| 3 | Toluene, hexanes | 15, 15 | 99.17 |
| 4 | Toluene, hexanes | 20, 10 | 99.25 |
| 5 | Toluene, hexanes | 10, 10 | 99.40 |

Example 5

Montelukast cyclohexylamine salt suspended in toluene (5 parts) was treated with aqueous acetic acid (5 parts) until a pH of 5.0~5.5 was reached. The organic phase was separated and washed with water (5 parts) twice, and the resulting organic layer was concentrated to provide a crude oil of montelukast acid. The montelukast acid (100.0 g, 170.2 mmol) thus obtained was dissolved in 500 mL THF, and then 78 mL of ca. 2N NaOH aqueous solution was added under nitrogen. After stirring for several minutes, the solvent was removed under reduced pressure at 30° C. to afford montelukast sodium as a crude oil. The crude oil was taken up in 2.5 L water and concentrated to remove the remaining THF until the total volume was about 2.7 L (THF remained as analyzed by GC was 1.7%). The aqueous solution of montelukast sodium was filtered, and its purity was determined by HPLC (99.7%). The filtered solution was subjected to spray drying at various conditions, and the results were listed in Table 5.

TABLE 5

Spray drying of montelukast sodium in aqueous solution

| | Feeding | | | Results | | | |
|---|---|---|---|---|---|---|---|
| Entry | rate mL/min | Inlet air (° C.) | Outlet air (° C.) | Purity HPLC % | THF (ppm) | KF (%) | Yield % |
| 1 | 20 | 140 | 100 | 99.7 | 92 | 1.9 | 60% |
| 2 | 20 | 150 | 100 | 99.7 | 89 | 1.7 | 60% |
| 3 | 28 | 140 | 85 | 99.1 | ND | 2.1 | 60% |
| 4 | 28 | 140 | 85 | 99.7 | ND | 1.6 | 60% |
| 5 | 28 | 150 | 84 | 99.6 | ND | 2.8 | 67% |
| 6 | 38 | 140 | 80 | 99.7 | ND | 2.7 | 50% | a. Spray drying is performed on Ohkawara Kakohki Co. Ltd model L-8
b. Solid content defined as the amount of solute is 4%
c. Solid obtained with bulk density 0.16 g/mL
d. Viscosity is 5.63 centistokes at 30° C. for 4% solid content
e. Aqueous solution density is about 1.0 g/mL
f. Particle size distribution; d (50) = 10 μm and d (90) = 30 μm

Example 6

Purified montelukast acid (85 mmol) was treated with 248 mL 0.31 N (77 mmol) sodium methoxide methanol solution (previously degassed), and additional 16.5 mL sodium methoxide was added until a pH of 8.43 was obtained. Most of the methanol was then removed under reduced pressure at less than 50° C. Water was added to the resulting crude oil, and the residual methanol was distilled off. Additional water was added to a final volume of 1,060 mL. The aqueous solution was then filtered, the residual methanol being 3.0% as determined by GC and the purity being 99.8% as determined by HPLC. The aqueous montelukast sodium was subjected to spray drying, and the results were listed in Table 6.

TABLE 6

Spray drying of montelukast sodium in aqueous solution

| | Feeding | | | Results | | | |
|---|---|---|---|---|---|---|---|
| Entry | rate mL/min | Inlet air (° C.) | Outlet air (° C.) | Purity HPLC % | MeOH (ppm) | KF (%) | Yield % |
| 1 | 20 | 120 | 80~85 | 99.8 | 0.00 | 1.8 | 80% |
| 2 | 30 | 140 | 78~80 | 99.7 | 0.00 | 2.2 | 90% |

While the invention has been described and exemplified in sufficient detail for those skilled in the art to make use of it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A compound of formula III which is represented as

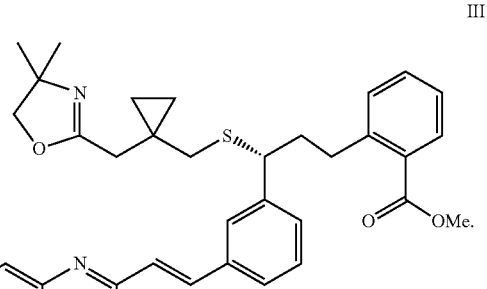

2. A compound of formula IV which is represented as

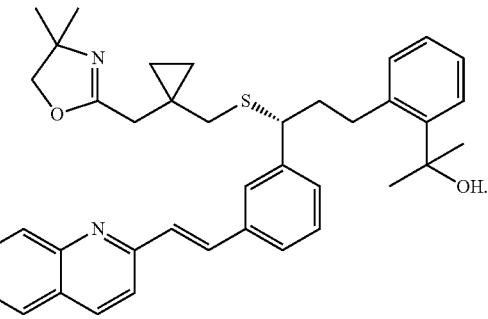

* * * * *